United States Patent
Iyengar et al.

[11] Patent Number: 6,017,930
[45] Date of Patent: Jan. 25, 2000

[54] METHODS OF TREATING OR PREVENTING INTERSTITIAL CYSTITIS

[75] Inventors: Smriti Iyengar; Mark A. Muhlhauser, both of Indianapolis, Ind.; Karl B. Thor, Morrisville, N.C.

[73] Assignee: Eli Lilly and Company, Indianapolis, Ind.

[21] Appl. No.: 09/125,952

[22] PCT Filed: Mar. 7, 1997

[86] PCT No.: PCT/US97/03555

§ 371 Date: Aug. 25, 1998

§ 102(e) Date: Aug. 25, 1998

[87] PCT Pub. No.: WO97/33583

PCT Pub. Date: Sep. 18, 1997

Related U.S. Application Data

[60] Provisional application No. 60/013,130, Mar. 11, 1996.

[51] Int. Cl.[7] .................................................. A61K 31/445
[52] U.S. Cl. ............................ 514/316; 514/323; 546/187
[58] Field of Search ...................................... 514/316, 323

[56] References Cited

PUBLICATIONS

The Journal of Urology, vol. 153, "Characterization of Tachykinin NK2 Receptors in Human Urinary Bladder," pp. 1688–1692 (1995).

*Primary Examiner*—Robert Gerstl
*Attorney, Agent, or Firm*—Elizabeth A. Dawalt; Paul J. Gaylo

[57] ABSTRACT

This invention provides methods for the treatment or prevention of interstitial cystitis or urethral syndrome in a mammal which comprise administering to a mammal in need thereof an effective amount of a compound of formula (I), where $R^1$ and $R^2$ are independently selected from the group consisting of hydrogen, methyl, methoxy, chloro, and trifluoromethyl, with the proviso that no more than one of $R^1$ and $R^2$ can be hydrogen; and Y is (1), (2), (3), (4), (5), (6), N—$R^a$, or CH—$NR^bR^c$, where $R^a$, $R^b$, and $R^c$ are independently selected from the group consisting of hydrogen and $C_1$–$C_6$ alkyl; or a pharmaceutically acceptable salt or solvate thereof.

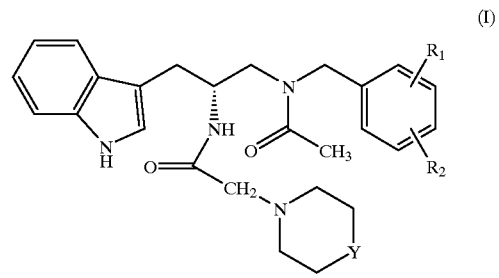

(I)

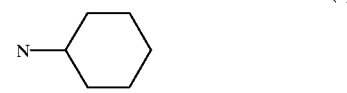

(1)

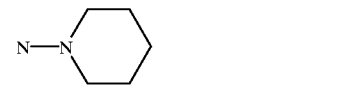

(2)

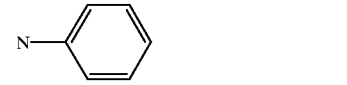

(3)

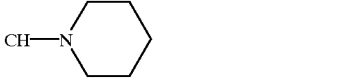

(4)

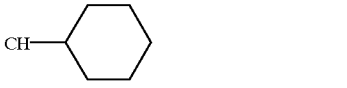

(5)

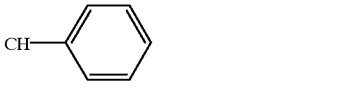

(6)

4 Claims, No Drawings

METHODS OF TREATING OR PREVENTING INTERSTITIAL CYSTITIS

This application claims benefit of Provisional Appln. No. 60/013,130 filed Mar. 11, 1996.

BACKGROUND OF THE INVENTION

Tachykinins are a family of peptides which share a common amidated carboxy terminal sequence. Substance P was the first peptide of this family to be isolated, although its purification and the determination of its primary sequence did not occur until the early 1970's.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). SEE J. E. Maggio, Peptides, 6 (Supplement 3):237–243 (1985) for a review of these discoveries.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches. See. e.g., S. L. Shepheard, et al., *British Journal of Pharmacology*, 108:11–20 (1993); S. M. Moussaoui, et al., *European Journal of Pharmacology*, 238:421–424 (1993); and W.S. Lee, et al., *British Journal of Pharmacology*, 112:920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in U.S. Pat. No. 5,328,927, issued Jul. 12, 1994; U.S. Pat. No. 5,360,820, issued Nov. 1, 1994; U.S. Pat. No. 5,344,830, issued Sep. 6, 1994; U.S. Pat. No. 5,331,089, issued Jul. 19, 1994; European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; and Patent Cooperation Treaty publication WO 93/011609, published Jan. 21, 1993.

Interstitial cystitis is a chronic debilitating inflammatory disorder of the bladder. The disease is most common in women ranging in age from about thirty to sixty with onset of the condition typically occurring at about forty years of age. It is characterized by a number of urinary difficulties, such as suprapubic pressure and pain, with bladder filling, urinary frequency, nocturia, dysuria, urgency adn irritative voiding associated with morphological and histological changes in the bladder. The condition is characterized as "interstitial cystitis" because it is believed the condition does not affect the surface of the bladder, but instead involves the spaces between the cells, namely the interstices, in the lining of the bladder.

Urethral syndrome is a related painful voiding disorder of unknown etiology affecting women exhibiting many of the conditions set forth above.

As noted in U.S. Pat. No. 5,145,859, issued Sep. 8, 1992, the entire contents of which are herein incorporated by reference, there are a number of compounds proposed to treat these conditions, based on differing theories as to the etiology of interstitial cystitis and urethral syndrome. None of these treatment regimens has proven completely successful to date.

Because of the current dissatisfaction of the currently marketed treatments for interstitial cystitis within the affected population, there exists a need for a more efficacious and safe treatment.

SUMMARY OF THE INVENTION

This invention provides methods for the treatment or prevention of interstitial cystitis or urethral syndrome in a mammal which comprise administering to a mammal in need thereof an effective amount of a compound of Formula I

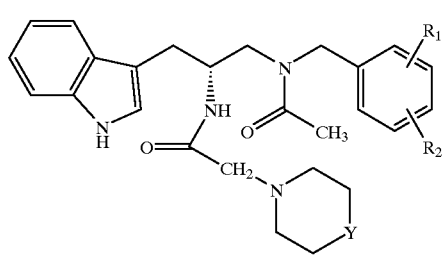

where
$R^1$ and $R^2$ are independently selected from the group consisting of hydrogen, methyl, methoxy, chloro, and trifluoromethyl, with the proviso that no more than one of $R^1$ and $R^2$ can be hydrogen; and
Y is

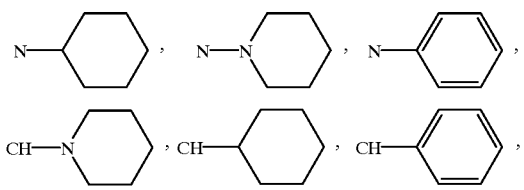

N—$R^a$, or CH—N$R^b R^c$,
where
$R^a$, $R^b$, and $R^c$ are independently selected from the group consisting of hydrogen and $C_1$–$C_6$ alkyl;

or a pharmaceutically acceptable salt or solvate thereof.

DETAILED DESCRIPTION AND PREFERRED EMBODIMENTS

The terms and abbreviations used in the instant examples have their normal meanings unless otherwise designated. For example "° C." refers to degrees Celsius; "N" refers to normal or normality; "mol" refers to mole or moles; "mmol" refers to millimole or millimoles; "g" refers to gram or grams; "kg" refers to kilogram or kilograms; "L" refers to liter or liters; "ml" means milliliter or milliliters; "M" refers to molar or molarity; "MS" refers to mass spectrometry; and "NMR" refers to nuclear magnetic resonance spectroscopy.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_3$ alkyl".

"Halo" represents chloro, fluoro, bromo or iodo.

The term "haloformate" as used herein refers to an ester of a haloformic acid, this compound having the formula

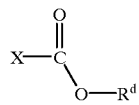

wherein X is halo, and $R^d$ is $C_1$–$C_6$ alkyl. Preferred haloformates are bromoformates and chloroformates. Especially preferred are chloroformates. Those haloformates wherein $R^d$ is $C_3$–$C_6$ alkyl are especially preferred. Most preferred is isobutylchloroformate.

The compounds prepared in the processes of the present invention have an asymmetric center. As a consequence of this chiral center, the compounds produced in the present invention may occur as racemates, mixtures of enantiomers and as individual enantiomers, as well as diastereomers and mixtures of diastereomers. Processes for preparing such asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockise relationship of group priorities (highest to second lowest) when viewed along the bond toward the lowest priority group. The priority of groups is based upon their atomic number (in order of decreasing atomic number). A partial list of priorities and a discussion of stereochemistry is contained in *NOMENCLATURE OF ORGANIC COMPOUNDS: PRINCIPLES AND PRACTICE*, (J. H. Fletcher, et al, eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

The term "treating" (or "treat") as used herein includes its generally accepted meaning which encompasses prohibiting, preventing, restraining, and slowing, stopping, or reversing progression, severity, or a resultant symptom. As such, the methods of this invention encompass both therapeutic and prophylactic administration.

Patent Cooperation Treaty Publication WO 95/14017, published May 26, 1995, teaches, inter alia, a series of tachykinin receptor antagonists of Formula II

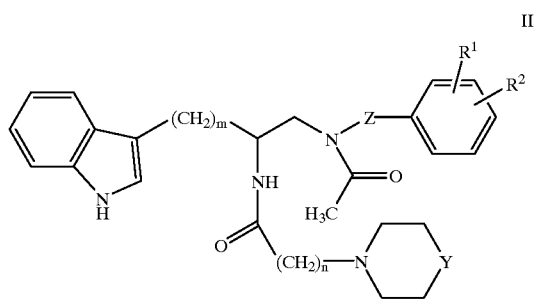

wherein:
  m and n are independently 0–6;
  Z is —$(CHR^4)_p$—$(CHR^6)_q$—, where,
    p is 0 or 1;
    q is 0 or 1; and
    $R^4$ and $R^6$ are independently selected from the group consisting of hydrogen and $C_1$–$C_3$ alkyl;
  Y is

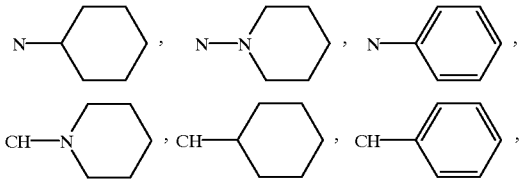

N—$R^a$, or CH—$NR^bR^c$,
  where
    $R^a$, $R^b$, and $R^c$ are independently selected from the group consisting of hydrogen and $C_1$–$C_6$ alkyl; and
    $R^1$ and $R^2$ are independently hydrogen, halo, $C_1$–$C_6$ alkoxy, $C_1$–C6 alkylthio, nitro, trifluoromethyl, or $C_1$–$C_6$ alkyl;
or a pharmaceutically acceptable salt or solvate thereof. These compounds have been shown to be very active, specific tachykinin receptor antagonists. Particularly preferred compounds are those of Formula II in which m and n are both 1; $R^1$ and $R^2$ are independently hydrogen, methoxy, ethoxy, chloro, fluoro, trifluoromethyl, methyl, and ethyl; Z is methylene; and Y, when combined with the heterocyclic group to which it is attached, forms 4-(piperidin-1-yl) piperidin-1-yl, 4-(cydohexyl)piperazin-1-yl, 4-(phenyl) piperazin-1-yl, or 4-(phenyl)piperidin-1-yl.

Especially preferred is the compound (R)-3-(1H-indol-3-yl)-1-[N-(2-methoxybenzyl)acetylamino]-2-[N-(2-(4-(piperidin-1-yl)piperidin-1-yl)acetyl)amino]propane and the pharmaceutically acceptable salts and solvates thereof. Most especially preferred is the compound (R)-3-(1H-indol-3-yl)-1-[N-(2-methoxybenzyl)acetylarino]-2-[N-(2-(4-(piperidin-1-yl)piperidin-1-yl)acetyl)amino]propane dihydrochloride trihydrate.

The most preferred method of synthesizing this compound is depicted in Scheme I, infra. Many of the steps of this synthesis are described in Patent Cooperation Treaty Publication WO 95/14017, published May 26, 1995, and European Patent Application Publication 693,489, published Jan. 24, 1996.
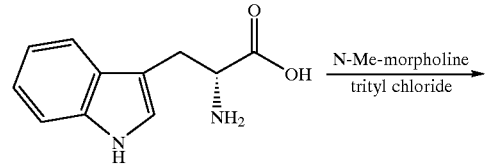
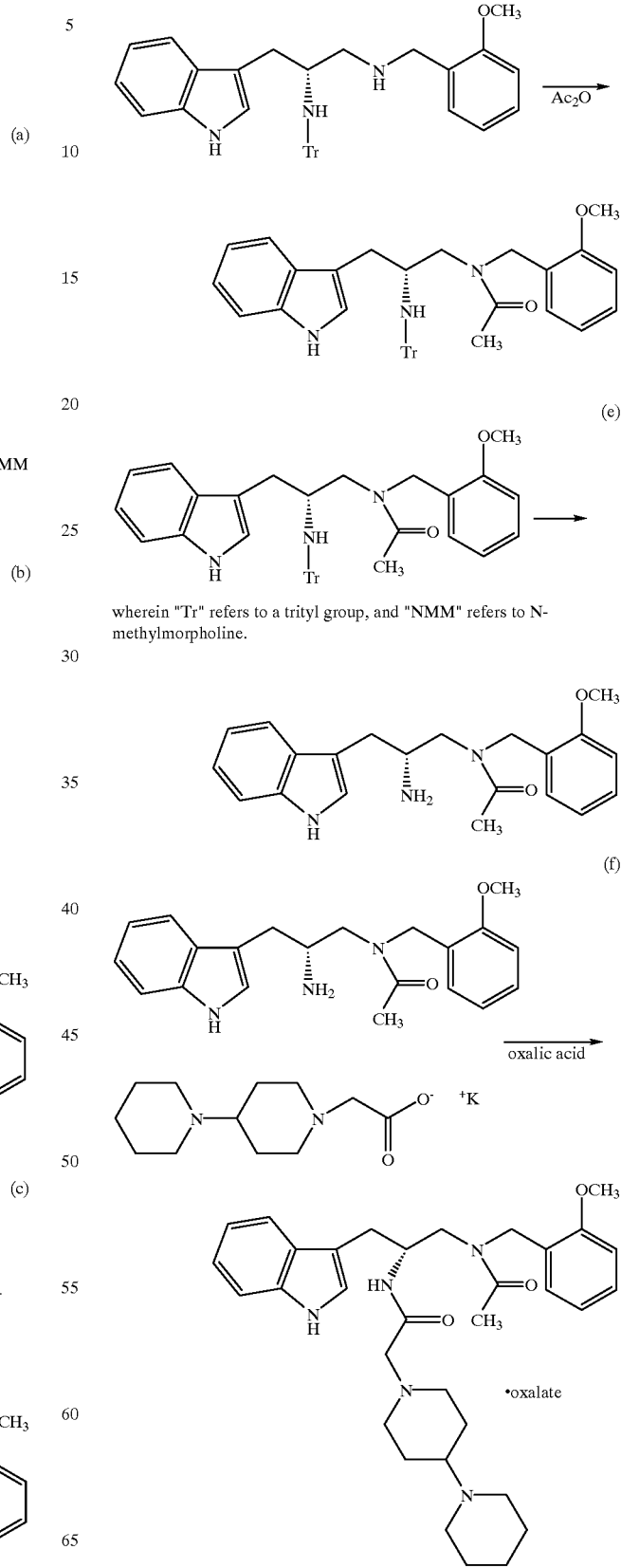
wherein "Tr" refers to a trityl group, and "NMM" refers to N-methylmorpholine.

Synthesis of (R)-2-[N-(2-((4-cyclohexyl)piperazin-1-yl)acetyl)amino]-3-(1H-indol-3-yl)-1-[N-(2-methoxybenzyl)acetylamino]propane (a) Preparation of (R)-3-(1H-indol-3-yl)-2-(N-triphenylmethylamino)propanoic acid [N-trityltryptophan]

Tritylation

Chlorotrirethyisilane (70.0 ml, 0.527 mol) was added at a moderate rate to a stirred slurry of D-tryptophan (100.0 g, 0.490 mol) in anhydrous methylene chloride (800 ml) under a nitrogen atmosphere. This mixture was continuously stirred for 4.25 hours. Triethylamine (147.0 ml, 1.055 mol) was added, followed by the addition of a solution of triphenylmethyl chloride (147.0 g, 0.552 mol) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous work-up involving a 5% citric acid solution (2×) and brine (2×) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mol) of analytically pure (R)-3-(1H-indol-3-yl)-2-(N-triphenylmethylamino) propanoic acid was isolated as a white solid in two crops giving a total of 79% yield.

FDMS 446 (M$^+$). $^1$H NMR (DMSO-d$_6$) δ 2.70 (m, 1H), 2.83 (m, 2H), 3.35 (m, 1H), 6.92–7.20 (m, 12H), 7.30–7.41 (m, 8H), 10.83 (s, 1H), 11.73 (br s, 1H).

Analysis for $C_{30}H_{26}N_2O_2$: Theory: C, 80.69; H, 5.87; N, 6.27. Found: C, 80.47; H, 5.92; N, 6.10.

(b) Preparation of (R)-3-(1H-indol-3-yl)-N-(2-methoxybenzyl)-2-(N-triphenylmethylamino) propanamide Coupling -continued

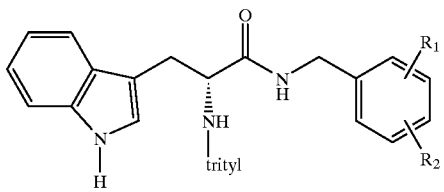

To a stirred solution of (R)-3-(1H-indol-3-yl)-2-(N-triphenylmethylamino)propanoic acid (179.8 g, 0.403 mol), 2-methoxybenzylamine (56.0 ml, 0.429 mol), and hydroxybenzotriazole hydrate (57.97 g, 0.429 mol) in anhydrous tetrahydrofuran (1.7 L) and anhydrous N,N-dimethylformamide (500 ml) under a nitrogen atmosphere at 0° C., were added triethylamine (60.0 ml, 0.430 mol) and 1-(3-dimethylaminopropyl)-3-ethoxycarbodiimide hydrochloride (82.25 g, 0.429 mol). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2x), saturated sodium bicarbonate solution (2x), and brine (2x) was performed. The organic layer was dried over anhydrous sodium sulfate and concentrated to dryness on a rotary evaporator. The desired product was then recrystallized from hot ethyl acetate to yield 215.8 g (0.381 mol, 95%) of analytically pure material.

FDMS 565 M+). $^1$H NMR (CDCl$_3$) δ 2.19 (dd, J=6.4 Hz, Δυ=14.4 Hz, 1H), 2.64 (d, J=6.5 Hz, 1H), 3.19 (dd, J=4.3 Hz, Δυ=14.4 Hz, 1H), 3.49 (m, 1H), 3.63 (s, 3H), 3.99 (dd, J=5.4 Hz, Δυ=14.2 Hz, 1H), 4.25 (dd, J=7.1 Hz, Δυ=14.2 Hz, 1H), 6.64 (d, J=2.1 Hz, 1H), 6.80 (d, J=8.2 Hz, 1H), 6.91 (t, J=7.4 Hz, 1H), 7.06–7.38 (m, 21H), 7.49 (d, J=7.9 Hz, 1H), 7.75 (s, 1H).

Analysis for $C_{38}H_{35}N_3O_2$: Theory: C, 80.68; H, 6.24; N, 7.43. Found: C, 80.65; H, 6.46; N, 7.50.

(c) Preparation of (R)-3-(1H-indol-3-yl)-1-[N-(2-methoxybenzyl)amino]-2-(N-triphenylmethylaino) propane
Reduction of Carbonyl

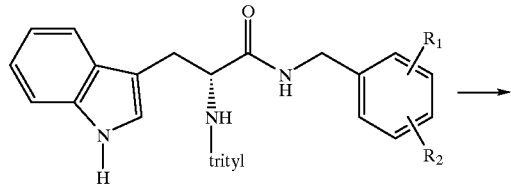

RED-AL®, [a 3.4 M, solution of sodium bis(2-methoxyethoxy)aluminum hydride in toluene] (535 ml, 1.819 mol), dissolved in anhydrous tetrahydrofuran (400 ml) was slowly added using an addition funnel to a refluxing solution of the acylation product, (R)-3-(1H-indol-3-yl)-N-(2-methoxybenzyl)-2-(N-triphenylmethylamino) propanamide (228.6 g, 0.404 mols) produced supra, in anhydrous tetrahydrofuran (1.0 L) under a nitrogen atmosphere. The reaction mixture became a purple solution. The reaction was quenched after at least 20 hours by the slow addition of excess saturated Rochelle's salt solution (potassium sodium tartrate tetrahydrate). The organic layer was isolated, washed with brine (2x), dried over anhydrous sodium sulfate, filtered, and concentrated to an oil on a rotary evaporator. No further purification was done and the product was used directly in the next step.

(d) Preparation of (R)-3-(1H-indol-3-yl)-1-[N-(2-5 methoxybenzyl)-acetylamino]-2-(N-triphenylmethylamino)propane
Acylation of Secondary Amine

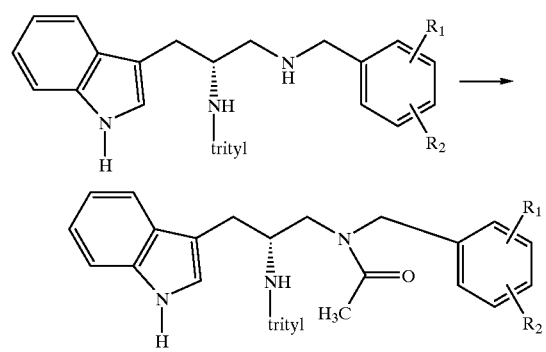

To a string solution of (R)-3-(1H-indol-3-yl)-1-[N-(2-methoxybenzyl)amino]-2-(N-triphenylmethylamino) propane (0.404 mol) in anhydrous tetrahydrofuran (1.2 L) under a nitrogen atmosphere at 0° C. was added triethylamine (66.5 ml, 0.477 mol) and acetic anhydride (45.0 ml, 0.477 mol). After 4 hours, the mixture was concentrated on a rotary evaporator, redissolved in methylene chloride and ethyl acetate, washed with water (2x) and brine (2x), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of (R)-3-(1H-indol-3-yl)-1-[N-(2-methoxybenzyl) acetylaminol]-2-(N-triphenylmethylam o)propane was crystallized and isolated over three crops giving 208.97 grams (87% yield) of analytically pure material.

Analysis for $C_{40}H_{39}N_3O_2$: Theory: C, 80.91; H, 6.62; N, 7.08. Found: C, 81.00; H, 6.69; N, 6.94.

(e) Preparation of (R)-2-amino-3-(1H-indol-3-yl)-1-[N-(2-methoxybenzyl)acetylamino]propane
Deprotection

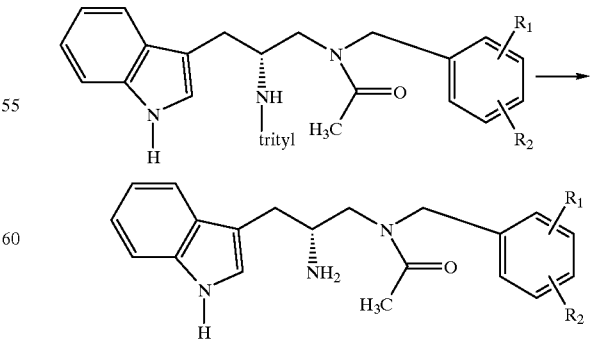

Formic acid (9.0 ml, 238.540 mmol) was added to a stirring solution of (R)-3-(1H-indol-3-yl)-1-[N-(2- methoxybenzyl)acetylamino]-2-(N-triphenylmethylamino) propane (14.11 g, 23.763 mmol) in anhydrous methylene chloride under a nitrogen atmosphere at 0° C. After 4 hours, the reaction mixture was concentrated to an oil on a rotary evaporator and redissolved in diethyl ether and 1.0 N hydrochloric acid. The aqueous layer was washed twice with diethyl ether and basified with sodium hydroxide to a pH greater than 12. The product was extracted out with methylene chloride (4x). The organic extracts were combined, dried over anhydrous sodium sulfate, filtered, and concentrated on a rotary evaporator to a white foam. The compound (R)-2-amino-3-(1H-indol-3-yl)-1-[N-(2-methoxybenzyl) acetylamino]propane (7.52 g, 21.397 mmols) was isolated giving a 90% yield. No further purification was necessary.

(f) Preparation of (R)-2-amino-3-(1H-indol-3-yl)-1-[N-(2-methoxybenzyl)acetylamino]propane dihydrochloride

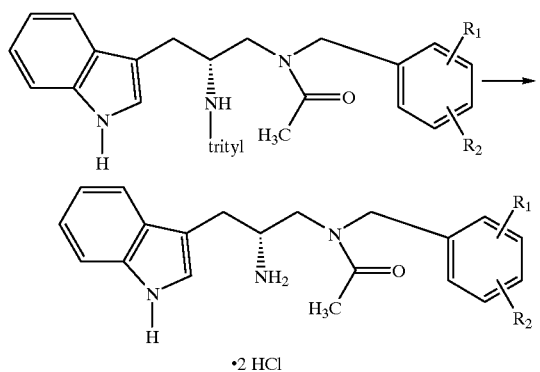

A stirring solution of (R)-3-(1H-indol-3-yl)-1-[N-(2-methoxybenzyl)acetylmino]-2-(N-triphenylmethylamino) propane in two volumes of methylene chloride was cooled to between –40° C. and –50° C. Anhydrous hydrogen chloride gas was added at such a rate that the temperature of the reaction mixture did not exceed 0° C. The reaction mixture was stirred for 30 minutes to one hour at 0–10° C.

To this reaction mixture was added two volumes of methyl t-butyl ether and the resulting mixture was allowed to stir for 30 minutes to one hour at 0–10° C. The resulting crystalline solid was removed by filtration and then washed with methyl t-butyl ether. The reaction product was dried under vacuum at 50° C. (Yield >98%)

Analysis for $C_{21}H_{25}N_3O_2 \cdot 2HCl$: Theory: C, 59.44; H, 6.41; N, 9.90. Found: C, 60.40; H, 6.60; N, 9.99.

(g) Preparation of 2-((4-cyclohexyl)piperazin-1-yl)acetic acid potassium salt hydrate Cyclohexylpiperazine (10.0 g, 0.059 mol) was added to ten volumes of methylene chloride at room temperature. To this mixture was added sodium hydroxide (36 ml of a 2N solution, 0.072 mol) and tetrabutylammonium bromide (1.3 g, 0.004 mol). After the addition of the sodium hydroxide and tetrabutylammonium bromide, methyl bromoacetate (7.0 ml, 0.073 mol) was added and the reaction mixture was stirred for four to six hours. The progress of the reaction was monitored by gas chromatography.

The organic fraction was separated and the aqueous phase was back-extracted with methylene chloride. The organic phases were combined and washed twice with deionized water, once with saturated sodium bicarbonate solution, and then with brine. The organic phase was dried over magnesium sulfate and the solvents were removed in vacuo to yield methyl 2-((4-cylohexyl)piperazin-1-yl)acetate as a yellowish oil.

The title compound was prepared by dissolving the methyl 2-((4-cyclohexyl)piperazin-1-yl)acetate (10.0 g, 0.042 mol) in ten volumes of diethyl ether. This solution was cooled to 15° C. and then potassium trimethylsilanoate (5.9 g, 0.044) was added. This mixture was then stirred for four to six hours. The reaction product was removed by filtration, washed twice with five volumes of diethyl ether, then washed twice with five volumes of hexanes, and then dried in a vacuum oven for 12–24 hours at 50° C.

Analysis for $C_{12}H_{21}KN_2O_2 \cdot 1.5 H_2O$: Theory: C, 49.63; H, 7.98; N, 9.65. Found: C, 49.54; H, 7.72; N, 9.11.

(h) Preparation of (R)-2-[N-(2-((4-cyclohexyl)piperazin-1-yl)acetyl)amino]-3-(1H-indol-3-yl)-1-[N-(2-methoxybenzyl)acetylamino]propane The title compound was prepared by first cooling 2-((4-cyclohexyl)piperazin-1-yl)acetic acid potassium salt to a temperature between –8° C. and –15° C. in 5 volumes of anhydrous methylene chloride. To this mixture was added isobutylchloroformate at a rate such that the temperature did not exceed –8° C. The resulting reaction mixture was stirred for about 1 hour, the temperature being maintained between –8° C. and –15° C.

To this mixture was then added (R)-2-amino-3-(1H-indol-3-yl)-1-[N-(2-methoxybenzyl)acetylamino]propane dihydrochloride at such a rate that the temperature did not exceed 0° C. Next added to this mixture was N-methyl morpholine at a rate such that the temperature did not exceed 0° C. This mixture was then stirred for about 1 hour at a temperature between –15° C. and –8° C.

The reaction was quenched by the addition of 5 volumes of water. The organic layer was washed once with a saturated sodium bicarbonate solution. The organic phase was then dried over anhydrous potassium carbonate and filtered to remove the drying agent. To the filtrate was then added 2 equivalents of concentrated hydrochloric acid, followed by 1 volume of isopropyl alcohol. The methylene chloride was then exchanged with isopropyl alcohol under vacuum by distillation.

The final volume of isopropyl alcohol was then concentrated to three volumes by vacuum. The reaction mixture was cooled to 20° C. to 25° C. and the product was allowed to crystallize for at least one hour. The desired product was then recovered by filtration and washed with sufficient isopropyl alcohol to give a colorless filtrate. The crystal cake was then dried under vacuum at 50° C. MS 560 (M+1$^+$).

$^1$H NMR (CDCl$_3$) δ 1.09–1.28 (m, 5H), 1.64 (d, J=10 Hz, 1H), 1.80–1.89 (m, 4H), 2.10 (s, 3H), 2.24–2.52 (m, 9H), 2.90 (s, 2H), 2.95 (d, J=7 Hz, 1H), 3.02 (d, J=7 Hz, 1H), 3.12 (dd, J=5, 14 Hz, 1H), 3.77 (s, 3H), 4.01 (dd, J=10, 14 Hz, 1H), 4.49 (ABq, J=17 Hz, 43 Hz, 2H), 4.56 (m, 1H), 6.79–6.87 (m, 3H), 7.05–7.24 (m, 4H), 7.34–7.41 (m, 2H), 7.67 (d, J=8 Hz, 1H), 8.22 (s, 1H).

Analysis for $C_{33}H_{45}N_5O_3$: Theory: C, 70.81; H, 8.10; N, 12.51. Found: C, 70.71; H, 8.21; N, 12.42.

Synthesis of (R)-3-(1H-indol-3-yl)-1-[N-(2-methoxybenzyl)acetylamino]-2-[N-(2-(4-(piperidin-1-yl)piperidin-1-yl)acetyl)arino]propane

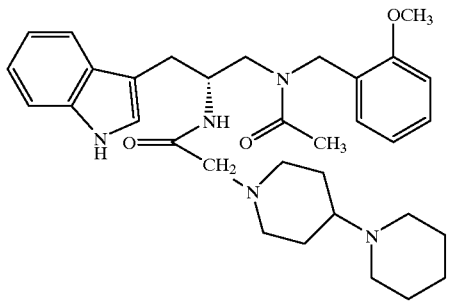

(a) Preparation of 2-(4-(piperidin-1-yl)piperidin-1-yl) acetic acid, potassium salt 4-(Piperidin-1-yl)piperidine (1.20 kg, 7.13 mol) was added to methylene chloride (12.0 L) under a nitrogen atmosphere. Tetrabutylammonium bromide (0.150 kg, 0.47 mol) and sodium hydroxide (1.7 L of a 5 N solution, 8.5 mol) were then added. The reaction mixture was cooled to 10–15° C. and methyl bromoacetate (1.17 kg, 7.65 mol) was added and the resulting mixture was stirred for a minimum of 16 hours.

Deionized water (1.2 L) was then added to the mixture and the layers separated. The aqueous layer was back-extracted with methylene chloride (2.4 L). The organic fractions were combined and washed with deionized water (3×1.2 L), a saturated sodium bicarbonate solution (1.1 L) and a saturated sodium chloride solution (1.1 L). The organic fraction was then dried over anhydrous magnesium sulfate and concentrated to an oil on a rotary evaporator to yield 1.613 kg (93.5%) of methyl 2-(4-(piperidin-1-yl)piperidin-1-yl)acetate.

A solution of methyl 2-[4-(piperidin-1-yl)piperidin-1-yl]acetate (2.395 kg, 9.96 mol) in methanol (2.4 L) was added to a solution of potassium hydroxide (0.662 kg, 10.0 mol @ 85% purity) in methanol (10.5 L) under a nitrogen atmosphere. The reaction mixture was heated to 45–50° C. for a minimum of 16 hours.

A solvent exchange from methanol to acetone (15.0 L) was performed on the solution on a rotary evaporator. This solution was slowly cooled to room temperature over 16 hours. The resulting solids were filtered, rinsed with acetone (5.0 L) and then dried to yield 2.471 kg (93.8%) of 2-(4-(piperidin-1-yl)piperidin-1-yl)acetic acid, potassium salt. MS 265 ($M^{+1}$)

(b) Preparation of (R)-3-(1H-indol-3-yl)-1-[N-(2-methoxybenzyl)acetylamino]-2-[N-(2-(4-(piperidin-1-yl)piperidin-1-yl)acetyl)amino]propane The title compound was prepared by first admixing (R)-2-amino-3-(1H-indol-3-yl)-1-[N-(2-methoxybenzyl)acetylaminolpropane dihydrochloride (50.0 g, 0.118 mol) with 100 ml of methylene chloride under a nitrogen atmosphere.

In a second flask, under a nitrogen atmosphere, 2-(4-(piperidin-1-yl)piperidin-1-yl)acetic acid potassium salt (62.3 g, 0.236 mol) was added to 600 ml of methylene chloride. This mixture was cooled to about −10° C. and stirring was continued. To this mixture isobutylchloroformate (23 ml, 0.177 mol) was added dropwise such that the temperature of the 2-(4-(piperidin-1-yl)piperidin-1-yl)acetic acid potassium salt mixture never rose appreciably.

This reaction mixture was stirred at about −10° C. for about 1.5 hours at which time the (R)-2-amino-3-(1H-indol-3-yl)-1-[N-(2-methoxybenzyl)acetylamino]propane dihydrochloride/methylene chloride mixture prepared supra was slowly added to the 2-(4-(piperidin-1-yl)piperidin-1-yl) acetic acid potassium salt/isobutylchloroformate/methylene chloride solution. The resulting mixture was then stirred for about 1 hour at a temperature between −15° C. and −8° C.

The reaction mixture was removed from the ice bath and allowed to warm to 15–20° C. and the reaction was quenched by the addition of 200 ml of water. The pH of the solution was adjusted to 2.3–2.7 by the addition of 1N sulfuric acid. The layers were separated and the aqueous layer was washed with 100 ml of methylene chloride.

The organic fractions were combined and washed with water (100 ml). The water wash was back extracted with methylene chloride (50 ml) and combined with the aqueous fraction from above. Methylene chloride (500 ml) was added to the combined aqueous layers and the mixture was stirred at room temperature for 15 minutes as basification with 2N sodium hydroxide to a final pH of 9.8 to 10.2 was achieved.

The organic and aqueous fractions were separated. The aqueous fraction was washed with methylene chloride and the methylene chloride was added to the organic fraction. The organic fraction was then washed with a mixture of saturated sodium bicarbonate solution (100 ml) and water (50 ml). The bicarbonate wash was separated from the organic fraction and back extracted with methylene chloride (50 ml). The back extraction was combined with the methylene chloride fraction and the combined fractions were dried over magnesium sulfate. The magnesium sulfate was removed by filtration and the volatiles were removed by vacuum distillation to yield the title product as a foam. (72.5 g, >98% yield). MS 559($M^{+1}$)

NMR (DMSO-$d_6$ 3:2 mixture of amide rotamers) δ 1.25–1.70 (m, 10H), 1.77–2.00 (m, 2H), 1.95 (s, 3/5•3H), 2.04 (s, 2/5•3H), 2.10–2.97 (m, 9H), 3.10–3.65 (m, 3H), 3.72 (s, 2/5•3H), 3.74 (s, 3/5•3H), 4.26–4.58 (m, 3H), 6.76–7.12 (m, 6H), 7.13–7.35 (m, 2H), 7.42–7.66 (m, 2H), 10.80 (br s, 1H).

Analysis for $C_{33}H_{45}N_5O_3$: Theory: C, 70.81; H, 8.10; N, 12.51. Found: C, 70.57; H, 8.05; N, 12.39.

An alternative process for preparing the compounds of Formula I follows.

Preparation of (R)-3-(1H-indol-3-yl)-2-(N-triphenylmethylamino)propanoic acid, N-methylmorpholine salt (N-trityl-D-tryptophan N-methylmopholine salt).

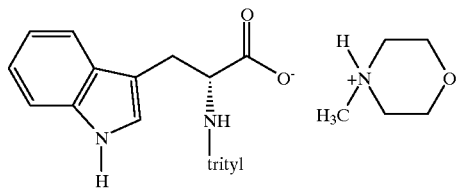

To a one liter 4 neck flask equipped with mechanical stirrer, condensor, probe, and stopper, were added D-tryptophan (40.0 g, 0.196 mol), acetonitrile (240 ml), and 1,1,1,3,3,3-hexamethyldisilazane (39.5 g, 0.245 mol). The resulting mixture was heated to 50–60° C. and stirred until homogeneous. In a separate beaker trityl chloride (60.06 g, 0.215 mol) and acetonitrile (120 ml) were slurried. The slurry was added to the silylated tryptophan mixture and the beaker was rinsed with 40 ml of acetonitrile. To the reaction mixture N-methylmorpholine (23.7 ml, 21.8 g, 0.216 mol) was added and the resulting mixture was stirred for one hour. The progress of the reaction was monitored by chromatography.

After satisfactory progress, water (240 ml) was added dropwise to the reaction mixture and the resulting mixture was cooled to less than 10° C., stirred for thirty minutes, and filtered. The residue was washed with water, and then dried to obtain 108.15 grams (>99% yield) of the desired title product.

$^1$H NMR (DMSO-d$_6$) δ 2.70 (m, 1H), 2.83 (m, 2H), 3.35 (m, 1H), 6.92–7.20 (m, 12H), 7.30–7.41 (m, 8H), 10.83 (s, 1H), 11.73 (br s, 1H).

Analysis for C$_{30}$H$_{26}$N$_2$O$_2$: Theory: C, 80.69; H, 5.87; N, 6.27. Found: C, 80.47; H, 5.92; N, 6.10.

Preparation of (R)-3-(1H-indol-3-yl)-N-(2-methoxybenzyl)-2-(N-triphenylmethylanmino)propanamide

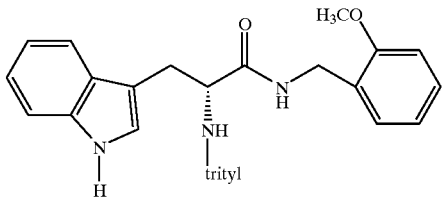

To a two liter 4 neck flask equipped with mechanical stirrer, condensor, and thermocouple, under a nitrogen atmosphere, were added N-trityl-D-tryptophan N-methylmopholine salt (108.0 g, 0.196 mol), acetonitrile (800 ml), 2-chloro-4,6-dimethoxy-1,3,5-triazine (38.63 g, 0.22 mol), and N-methylmorpholine (29.1 ml). The resulting mixture was stirred at ambient temperature until homogeneous (about ten minutes).

After about one hour, 2-methoxybenzylamine (29 ml) was added. The resulting mixture was heated to 35° C. and maintained at that temperature overnight. The progress of the reaction was monitored by chromatography. Water (750 ml) was then added dropwise to the reaction mixture and the resulting mixture was cooled to less than 10° C., stirred for thirty minutes, and filtered. The residue was washed with water (about 100 ml), and then dried to obtain the desired title product. (Yield: 87% and 91% in two runs)

FDMS 565 (M$^+$). $^1$H NMR (CDCl$_3$) δ 2.19 (dd, J=6.4 Hz, Δυ=14.4 Hz, 1H), 2.64 (d, J=6.5 Hz, 1H), 3.19 (dd, J=4.3 Hz, Δυ=14.4 Hz, 1H), 3.49 (m, 1H), 3.63 (s, 3H), 3.99 (dd, J=5.4 Hz, Δυ=14.2 Hz, 1H), 4.25 (dd, J=7.1 Hz, Δυ=14.2 Hz, 1H), 6.64 (d, J=2.1 Hz, 1H), 6.80 (d, J=8.2 Hz, 1H), 6.91 (t, J=7.4 Hz, 1H), 7.06–7.38 (m, 21H), 7.49 (d, J=7.9 Hz, 1H), 7.75 (s, 1H).

Analysis for C$_{38}$H$_{35}$N$_3$O$_2$: Theory: C, 80.68; H, 6.24; N, 7.43. Found: C, 80.65; H, 6.46; N, 7.50.

Reduction of Carbonyl

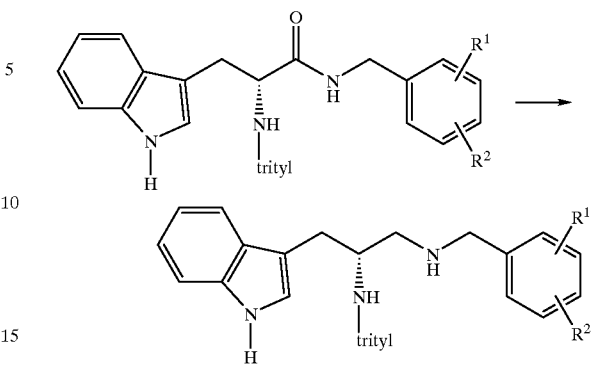

Preparation of (R)-3-(1H-indol-3-yl)-1-[N-(2-methoxybenzyl)amino]-2-(N-triphenylmethylamino)propane RED-AL™, [a 3.4 M, solution of sodium bis(2-methoxyethoxy)aluminum hydride in toluene] (535 ml, 1.819 mol), dissolved in anhydrous tetrahydrofuran (400 ml) was slowly added using an addition funnel to a refluxing solution of the acylation product, (R)-3-(1H-indol-3-yl)-N-(2-methoxybenzyl)-2-(N-triphenylmethylamino) propanamide (228.6 g, 0.404 mols) produced supra, in anhydrous tetrahydrofuran (1.0 L) under a nitrogen atmosphere. The reaction mixture became a purple solution. The reaction was quenched after at least 20 hours by the slow addition of excess saturated Rochelle's salt solution (potassium sodium tartrate tetrahydrate). The organic layer was isolated, washed with brine (2×), dried over anhydrous sodium sulfate, filtered, and concentrated to an oil on a rotary evaporator. No further purification was done and the product was used directly in the next step.

Acylation of Secondary Amine

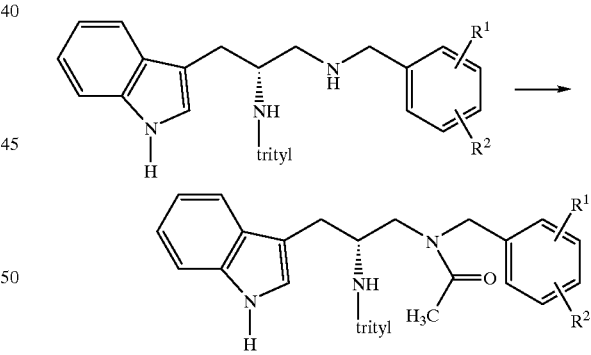

Preparation of (R)-3-(1H-indol-3-yl)-1-[N-(2-methoxybenzyl)-acetylamino]-2-(N-triphenylmethylamino)propane To a stirring solution of (R)-3-(1H-indol-3-yl)-1-[N-(2-methoxybenzyl)amino]-2-(N-triphenylmethylamino) propane (0.404 mol) in anhydrous tetrahydrofuran (1.2 L) under a nitrogen atmosphere at 0° C. was added triethylamine (66.5 ml, 0.477 mol) and acetic anhydride (45.0 ml, 0.477 mol). After 4 hours, the mixture was concentrated on a rotary evaporator, redissolved in methylene chloride and ethyl acetate, washed with water (2×) and brine (2×), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of (R)-3-(1H-indol-3-yl)-1-[N-(2-5 methoxybenzyl) acetylamino]-2-(N-triphenylmethylamino)propane was crystallized and isolated over three crops giving 208.97 grams (87% yield) of analytically pure material.

Analysis for $C_{40}H_{39}N_3O_2$: Theory: C, 80.91; H, 6.62; N, 7.08. Found: C, 81.00; H, 6.69; N, 6.94.

Deprotection

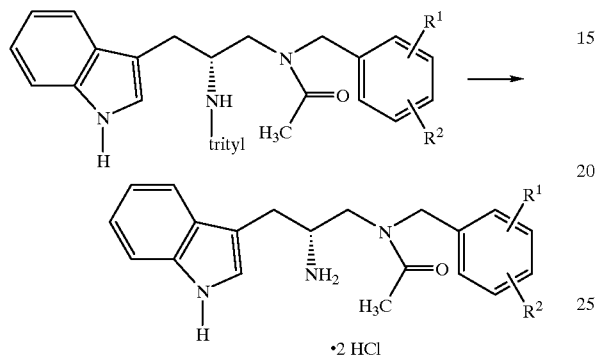

Preparation of (R)-2-amino-3-(1H-indol-3-yl)-1-[N-(2-methoxybenzyl)acetylamino]propane dihydrochloride A stirring solution of (R)-3-(1H-indol-3-yl)-1-[N-(2-methoxybenzyl)acetylamino]-2-(N-triphenylmethylamino) propane in two volumes of methylene chloride was cooled to between −40° C. and −50° C. Anhydrous hydrogen chloride gas was added at such a rate that the temperature of the reaction mixture did not exceed 0° C. The reaction mixture was stirred for 30 minutes to one hour at 0–10° C.

To this reaction mixture was added two volumes of methyl t-butyl ether and the resulting mixture was allowed to stir for 30 minutes to one hour at 0–10° C. The resulting crystalline solid was removed by filtration and then washed with methyl t-butyl ether. The reaction product was dried under vacuum at 50° C. (Yield >98%)

Analysis for $C_{21}H_{25}N_3O_2$•2 HCl: Theory: C, 59.44; H, 6.41; N, 9.90. Found: C, 60.40; H, 6.60; N, 9.99.

Preparation of 2-((4-cyclohexyl)piperazin-1-yl) acetic acid potassium salt hydrate Cydohexylpiperazine (10.0 g, 0.059 mol) was added to ten volumes of methylene chloride at room temperature. To this mixture was added sodium hydroxide (36 ml of a 2N solution, 0.072 mol) and tetrabutylammonium bromide (1.3 g, 0.004 mol). After the addition of the sodium hydroxide and tetrabutylammonium bromide, methyl bromoacetate (7.0 ml, 0.073 mol) was added and the reaction mixture was stirred for four to six hours. The progress of the reaction was monitored by gas chromatography.

The organic fraction was separated and the aqueous phase was back-extracted with methylene chloride. The organic phases were combined and washed twice with deionized water, once with saturated sodium bicarbonate solution, and then with brine. The organic phase was dried over magnesium sulfate and the solvents were removed in vacuo to yield methyl 2-((4-cyclohexyl)piperazin-1-yl)acetate as a yellowish oil.

The title compound was prepared by dissolving the methyl 2-((4-cyclohexyl)piperazin-1-yl)acetate (10.0 g, 0.042 mol) in ten volumes of diethyl ether. This solution was cooled to 15° C. and then potassium trimethylsilanoate (5.9 g, 0.044) was added. This mixture was then stirred for four to six hours. The reaction product was removed by filtration, washed twice with five volumes of diethyl ether, then washed twice with five volumes of hexanes, and then dried in a vacuum oven for 12–24 hours at 50° C.

Analysis for $C_{12}H_{21}KN_2O_2$•1.5 $H_2O$: Theory: C, 49.63; H, 7.98; N, 9.65. Found: C, 49.54; H, 7.72; N, 9.11.

Preparation of (R)-2-[N-(2-((4-cyclohexyl) piperazin-1-yl)acetyl)amino]-3-(1H-indol-3-yl)-1-[N-(2-methoxybenzyl)acetylamino]propane

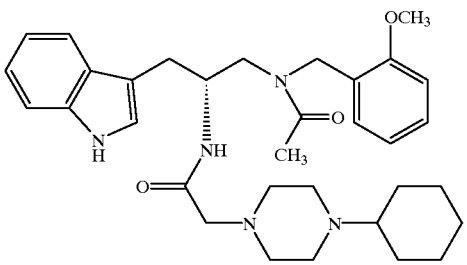

The title compound was prepared by first cooling 2-((4-cydohexyl)piperazin-1-yl)acetic acid potassium salt to a temperature between −8° C. and −15° C. in 5 volumes of anhydrous methylene chloride. To this mixture was added isobutylchloroformate at a rate such that the temperature did not exceed −8° C. The resulting reaction mixture was stirred for about 1 hour, the temperature being maintained between −8° C. and −15° C.

To this mixture was then added (R)-2-amino-3-(1H-indol-3-yl)-1-[N-(2-methoxybenzyl)acetylamino]propane dihydrochloride at such a rate that the temperature did not exceed 0° C. Next added to this mixture was N-methyl morpholine at a rate such that the temperature did not exceed 0° C. This mixture was then stirred for about 1 hour at a temperature between −15° C. and −8° C.

The reaction was quenched by the addition of 5 volumes of water. The organic layer was washed once with a saturated sodium bicarbonate solution. The organic phase was then dried over anhydrous potassium carbonate and filtered to remove the drying agent. To the filtrate was then added 2 equivalents of concentrated hydrochloric acid, followed by 1 volume of isopropyl alcohol. The methylene chloride was then exchanged with isopropyl alcohol under vacuum by distillation.

The final volume of isopropyl alcohol was then concentrated to three volumes by vacuum. The reaction mixture was cooled to 20° C. to 25° C. and the product was allowed to crystallize for at least one hour. The desired product was then recovered by filtration and washed with sufficient isopropyl alcohol to give a colorless filtrate. The crystal cake was then dried under vacuum at 50° C. MS 560 (M+1$^+$).

$^1$H NMR (CDCl$_3$) δ 1.09–1.28 (m, 5H), 1.64 (d, J=10 Hz, 1H), 1.80–1.89 (m, 4H), 2.10 (s, 3H), 2.24–2.52 (m, 9H), 2.90 (s, 2H), 2.95 (d, J=7 Hz, 1H), 3.02 (d, J=7 Hz, 1H), 3.12 (dd, J=5, 14 Hz, 1H), 3.77 (s, 3H), 4.01 (dd, J=10, 14 Hz, 1H), 4.49 (ABq, J=17 Hz, 43 Hz, 2H), 4.56 (m, 1H), 6.79–6.87 (m, 3H), 7.05–7.24 (m, 4H), 7.34–7.41 (m, 2H), 7.67 (d, J=8 Hz, 1H), 8.22 (s,1H).

Analysis for $C_{33}H_{45}N_5O_3$: Theory: C, 70.81; H, 8.10; N, 12.51. Found: C, 70.71; H, 8.21; N, 12.42.

Preparation of 2-(4-(piperidin-1-yl)piperidin-1-yl) acetic acid, potassium salt

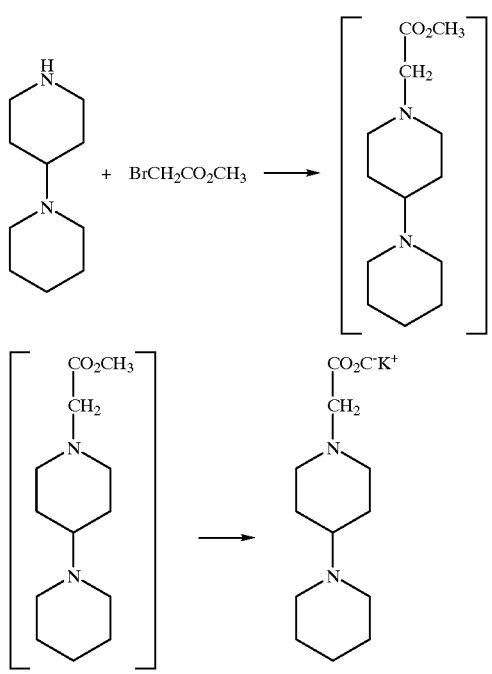

4-(Piperidin-1-yl)piperidine (1.20 kg, 7.13 mol) was added to methylene chloride (12.0 L) under a nitrogen atmosphere. Tetrabutylammonium bromide (0.150 kg, 0.47 mol) and sodium hydroxide (1.7 L of a 5 N solution, 8.5 mol) were then added. The reaction mixture was cooled to 10–15° C. and methyl bromoacetate (1.17 kg, 7.65 mol) was added and the resulting mixture was stirred for a minimum of 16 hours.

Deionized water (1.2 L) was then added to the mixture and the layers separated. The aqueous layer was back-extracted with methylene chloride (2.4 L). The organic fractions were combined and washed with deionized water (3×1.2 L), a saturated sodium bicarbonate solution (1.1 L) and a saturated sodium chloride solution (1.1 L). The organic fraction was then dried over anhydrous magnesium sulfate and concentrated to an oil on a rotary evaporator to yield 1.613 kg (93.5%/) of methyl 2-(4-(piperidin-1-yl) piperidin-1-yl)acetate.

A solution of methyl 2-[4-(piperidin-1-yl)piperidin-1-yl] acetate (2.395 kg, 9.96 mol) in methanol (2.4 L) was added to a solution of potassium hydroxide (0.662 kg, 10.0 mol @ 85% purity) in methanol (10.5 L) under a nitrogen atmosphere. The reaction mixture was heated to 45–50° C. for a minimum of 16 hours.

A solvent exchange from methanol to acetone (15.0 L) was performed on the solution on a rotary evaporator. This solution was slowly cooled to room temperature over 16 hours. The resulting solids were filtered, rinsed with acetone (5.0 L) and then dried to yield 2.471 kg (93.8%) of 2-(4-(piperidin-1-yl)piperidin-1-yl)acetic acid, potassium salt. MS 265 ($M^{+1}$)

Preparation of (R)-3-(1H-indol-3-yl)-1-[N-(2-methoxybenzyl)acetylamino]-2-[N-(2-(4-(piperidin-1-yl)piperidin-1-yl)acetyl)amino]propane dihydrochloride trihydrate

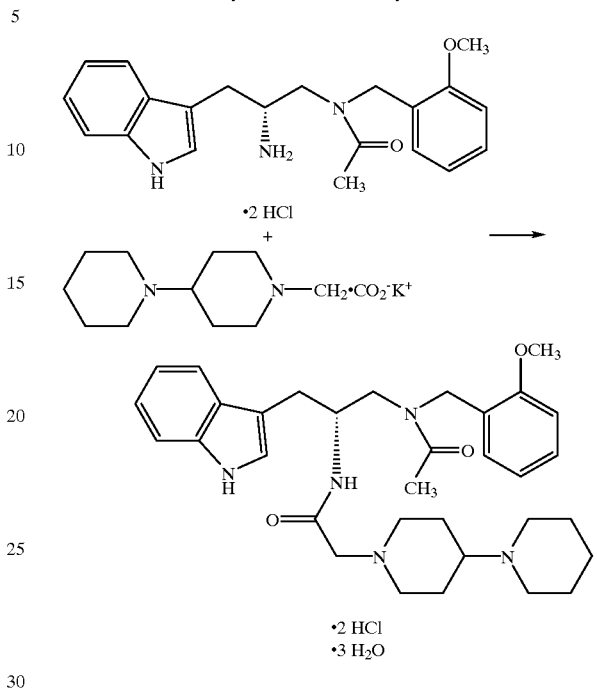

Under a nitrogen atmosphere 2-(4-(piperidin-1-yl) piperidin-1-yl)acetic acid, potassium salt (0.75 kg, 2.84 mol) was added to methylene chloride (7.5 L). The resulting mixture was cooled to −15 to −8° C. and isobutyl chloroformate (0.29 kg, 2.12 mol) was added at such a rate so as to maintain the temperature of the reaction mixture below −8° C. After the addition the resulting reaction mixture was stirred for 90 minutes between −15 and −8° C.

The reaction mixture was then cooled to −35° C. and solid (R)-2-amino-3-(1H-indol-3-yl)-1-[N-(2-methoxybenzyl) amino]propane dihydrochloride (0.60 kg, 1.14 mol) was added at such a rate that the reaction temperature was maintained at less than −20° C. After the addition, the reaction mixture was stirred for about one hour with the temperature being maintained between −37° C. and −20° C. The reaction was quenched by the addition of deionized water (7.5 L). The reaction mixture was basified to pH 12.8–13.2 by the addition of 5 N sodium hydroxide. The aqueous fraction was removed and retained. Additional deionized water (3.75 L) was added to the organic fraction as was sufficient 5 N sodium hydroxide to re-adjust the pH to 12.8–13.2.

The two aqueous fractions were combined, back-extracted with methylene chloride (1.5 L) and then discarded. The organic fractions were combined and washed with deionized water (4×3.5 L). These extracts were combined, back-extracted with methylene chloride (1.5 L), and then discarded. The two organic layers were combined and washed with a saturated sodium chloride solution (3.7 L).

The organic fraction was dried over anhydrous magnesium sulfate, filtered, and solvent exchanged from methylene chloride to acetone (3.75 L) on a rotary evaporator. An aqueous solution of hydrochloric acid (0.48 L of 6 N solution, 2.88 mol) and seed crystals (2 g) were added and mixture was stirred for 30–90 minutes. Acetone (13.2 L) was then added and the slurry stirred for one hour. The resulting solid was then filtered, washed with acetone (2×1.4 L), and dried to yield 633 g (90%) of (R)-3-(1H-indol-3-yl)-1-[N-(2-methoxybenzyl)acetylamino]-2-[N-(2-(4-(piperidin-1-yl)piperidin-1-yl)acetyl)amino]propane dihydrochloride trihydrate.

Preparation of (R)-3-(1H-indol-3-yl)-1-[N-(2-methoxybenzyl)acetylamino]-2-[-(2-(4-(piperidin-1-yl)piperidin-1-yl)acetyl)amino]propane dioxalate

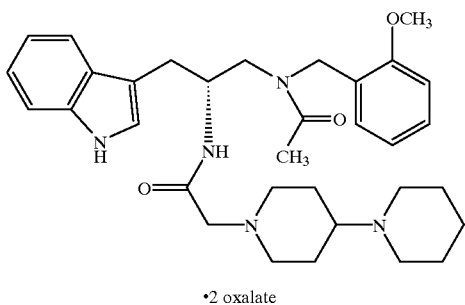

•2 oxalate

Into a 500 ml jacketed round bottom flask was placed 2-(4-(piperidin-1-yl)piperidin-1-yl)acetic acid, potassium salt (25.0 g, 94.5 mmol) and 375 ml of N,N-dimethylformamide. The resulting slurry was cooled to −19° C. and isobutylchloroformate (12.9 g, 94.5 mmol) was added over five minutes. The resulting mixture was stirred for twenty minutes and then (R)-2-amino-3-(1H-indol-3-yl)-1-[N-(2-methoxybenzyl)acetylamino]propane dihydrochloride (25.0 g, 58.1 mnmol), dissolved in 75 ml of anhydrous N,N-dimethylformamide, was added over ten minutes.

The resulting mixture is then cooled to 0° C., stirred for about ten minutes, and then permitted to warm to room temperature. The progress of the reaction was monitored by chromatography. High performance liquid chromatography showed 99% conversion of the reactants after ninety minutes.

The reaction mixture was partitioned between ethyl acetate (375 ml) and a saturated sodium bicarbonate solution (375 ml). The aqueous layer was back extracted with 375 ml of ethyl acetate. The organic fractions were combined, washed with water (3×375 ml), and then dried over magnesium sulfate. Potassium hydroxide is then added to the aqueous fraction from above and this resulting basified solution is extracted with ethyl acetate. This organic fraction is then dried over magnesium sulfate.

The combined dried organic fractions are then treated with a concentrated oxalic acid solution. The resulting solids are filtered and dried at 50° C. om a vacuum oven to yield 23.5 grams of the desired intermediate.

As would be appreciated by a skilled practitioner the mixed anhydride process will work in a number of organic solvents, in addition to the anhydrous N,N-dimethylformamide depicted above. Representative examples of solvents which may be employed include acetonitrile, tetrahydrofuran, dichloromethane. The mixed anhydride process can be performed at temperatures below 0° C.

The oxalate can be isolated from ethyl acetate as well as from other solvents, probably including acetone, acetonitrile, and t-butyl methyl ether. The use of oxalic acid is, however, very important for the precipitation as a large number of acids do not give a precipitate. Among those acids attempted, but found not satisfactory for the processes of the present invention, are citric, anhydrous hydrochloric, tartaric, mandelic, trifluoroacetic, p-nitrobenzoic, phenoxyacetic, maleic, fumaric, glutaric, adipic, methanesulfonic, p-toluenesulfonic, pamoic, trans-1,2-cyclohexane dicarboxylic, succinic, phthalic, trans-1,2-diaminocyclohexane-N,N,N',N'-naphthalenedisulfonic, and 5-sulfosalicylic acids. Only oxalic acid and 1,5-naphthalene disulfonic acid reproducibly produced a solid.

Preparation of R()-3-(1H-indol-3-yl)-1-[N-(2-methoxybenzyl)acetylamino]-2-[N-(2-(4-(piperidin-1-yl)piperidin-1-yl)acetyl)amino]propane dihydrochloride trihydrate

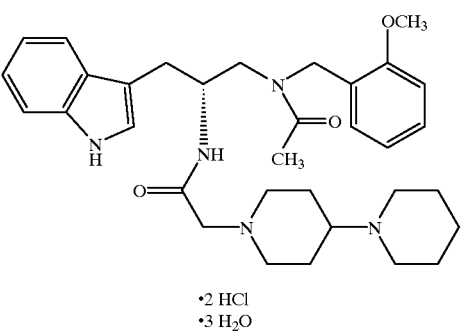

•2 HCl
•3 H$_2$O

Into a large beaker were added (R)-3-(1H-indol-3-yl)-1-[N-(2-methoxybenzyl)acetylamino]-2-[N-(2-(4-(piperidin-1-yl)piperidin 1-yl)acetyl)amino]propane dioxalate (13.4 g, 18.1 mmol), methylene chloride (58.16 ml, 78.51 g), and water (118.59 ml). The resulting mixture was stirred and the pH of the reaction mixture was adjusted to 10–12 using 50% caustic.

The phases were separated and the organic phase was back extracted with water (101.44 ml). The organic fraction was transferred to a jacketed round bottom flask and a solvent exchange was performed using about 23 volumes of acetone. Portions of the acetone were added to the product solution and the amount added was distilled away. The progress of the solvent exchange was monitored by NMR. The amount of desired product was monitored by high performance liquid chromatography.

Enough water was added to bring the water concentration to eleven percent and the resulting mixture was heated to 55° C. Enough concentrated hydrochloric acid was added to lower the pH to 2.0 and the reaction mixture was then permitted to cool to 37° C. over 45 minutes.

The product solution was seeded and permitted to stir for 10–30 minutes. The product solution was cooled to 19° C. over two hours and acetone (ten equivalent volumes) was added over three hours, after which time the reaction mixture was stirred for one to three hours, maintaining the temperature at 19° C. The product solution was filtered and the residue was washed with 6.67 equivalents of acetone. The residue was then dried in a vacuum oven at 42° C. to give the desired title product.

The other compounds of Formula I may be prepared essentially as described above, employing corresponding starting materials.

The biological efficacy of a compound believed to be effective as a tachykinin receptor antagonist may be confirmed by employing an initial screening assay which rapidly and accurately measured the binding of the tested compound to known NK-1 and NK-2 receptor sites. Assays useful for evaluating tachykinin receptor antagonists are well known in the art. See, e.g., J. Jukic, et al., *Life Sciences*, 49:1463–1469 (1991); N. Kucharczyk, et al., *Journal of Medicinal Chemistry*, 36:1654–1661 (1993); N. Rouissi, et al, *Biochemical and Biophysical Research Communications*, 176:894–901 (1991).

NK-1 Receptor Binding Assay

Radioreceptor binding assays were performed using a derivative of a previously published protocol. D. G. Payan, et al, *Journal of Immunology*, 133:3260–3265 (1984). In this assay an aliquot of IM9 cells ($1 \times 10^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See. e.g., *Annals of the New York Academy of Science*, 190: 221–234 (1972); *Nature (London)*, 251:443–444 (1974); *Proceedings of the National Academy of Sciences (USA)*, 71:84–88(1974). These cells were routinely cultured in RPMI 1640 supplemented with 50 µg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, were grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure, and the final pellets were resuspended in 100–120 ml 50 mM Tris buffer, pH 7.4, and 4 ml aliquots stored frozen at –70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 µg/ml chymostatin. A 200 µl volume of the homogenate (40 µg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 µl; the final concentration in the assay was 20 pM. Non-specific binding was determined using 1 µM eledoisin. Ten concentrations of eledoisin from 0.1 to 1000 nM were used for a standard concentration-response curve.

All samples and standards were added to the incubation in 10 µl dimethylsulfoxide (DMSO) for screening (single dose) or in 5 µl DMSO for IC$_{50}$ determinations. The order of additions for incubation was 190 or 195 µl assay buffer, 200 µl homogenate, 10 or 5 µl sample in DMSO, 100 µl radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 ml of cold 50 mM Tris buffer, pH 7.7. The filter circles were then punched into 12×75 mm polystyrene tubes and counted in a gamma counter.

It has been determined that the method of the present invention is effective in treating mammals, particularly middle-aged women, exhibiting symptoms of interstitial cystitis and/or urethral syndrome. In this regard, the clinical and local immune response to the compounds of the present invention is investigated in an open trail with 10female interstitial cystitis patients, whose disease is diagnosed according to the consensus criteria developed in 1987 at a National Institutes of Health workshop. To make objective the symptoms and the clinical response of the patients the present inventors scored (scale 0 to 2) the symptoms of frequency, urgency, nocturia, dysuria and suprapubic pain, as described in U.S. Pat. No. 5,145,859, issued Sep. 8, 1992, the entire contents of which are herein incorporated by reference. A compound of the present invention is administered as a single daily dose determined by a dose-titration test. Urinary interleukin-2 inhibitory activity (IL-2-IN), a marker of cell-mediated inflammation, is measured using a murine interleukin-2 dependent cell line.

The patients are reviewed for reduction in clinical symptoms. Drug side-effects are minimal. Urinary IL-2-IN activity before therapy confirms the presence of cell-mediated inflammation: after 4 months of therapy IL-2-IN activity is normal in most of the patients, regardless of the severity of symptoms, which indicates that the compounds of Formula I exerts an immunosuppressive effect. The data suggests that the compounds of Formula I can be an efficacious, well-tolerated, convenient oral medication for the treatment of interstitial cystitis.

In addition, as more dearly demonstrated below in Example 2, the present inventors also observes similar responses in regard to the treatment of urethral syndrome. As a result, the test data dearly indicates that the compounds employed in the present invention can be effective therapeutic agents for the treatment of interstitial cystitis and/or urethral syndrome.

As a result, it has been found that compounds of Formula I are particularly well-suited for the treatment of interstitial cystitis and/or urethral syndrome because they not only provide effective relief, are available for oral administration, and are relatively inexpensive. It has been discovered that patients receiving the compounds of Formula I substantially reduce the pathological conditions exhibited by these two pain bladder disorders, and are able to carry on their daily activities in a relatively normal existence in comparison with their pre-treatment state.

The present invention will be further described according to the following non-limiting examples.

EXAMPLE 1

Materials and Methods

Patients. The diagnosis of interstitial cystitis is assigned to 10 female patients, aged 23 to 51 years, in accordance with the consensus criteria established at the National Institutes of Health workshop on interstitial cystitis, August, 1987 (Gillenwater, J. Y. and Wein, A. J.: Summary of the National Institute of Arthritis, Diabetes, Digestive and Kidney Diseases Workshop on Interstitial Cystitis, National Institutes of Health, Bethesda, Md., Aug. 28–29, 1987, J. Urol., 140:203, 1988), and U.S. Pat. No. 5,145,859:

| Interstitial Cystitis: Criteria for Diagnosis | |
| --- | --- |
| Inclusion Criteria | Exclusion Criteria |
| Hunner's Ulcer (if present, automatic inclusion) | less than 18 years old benign or malignant tumors radiation, tuberculous, bacterial |
| Positive Factors (at least 2 required for inclusion): | or cyclophosphamide cystitis vaginitis duration of symptoms <1 year |
| suprapubic, pelvic, urethral, vaginal or perineal pain | gynecologic cancer urethral diverticulum, bladder or lower ureteral calculi |
| glomerulations at cystoscopy after bladder distension (80 cm water pressure × 1 min.) | active herpes (HSV II) waking frequency <5 in 12 hrs. nocturia <2 neurogenic bladder dysfunction |
| decreased compliance on cystometrogram | waking capacity >400 ml, absence of urgency with bladder filling symptoms relieved by antibiotics, urinary |
| pain on bladder filling relieved by emptying | urinary analgesics or antiseptics |

Cystometrics are performed after cessation of other modes of therapy and prior to institution of therapy: all patients had a waking bladder capacity of less than 350 ml (range 150 ml to 340 ml).

Symptom Evaluation: The symptom scores (total score range: 0 to 10) form the basis for the evaluation of treatment efficacy. The severity of each symptom is assigned a numerical value, as follows:

| Symptom Severity Survey | | |
| --- | --- | --- |
| Symptom | Description | Score |
| Frequency (daytime) | voids once every 3 to 5 hours | 0 |
|  | voids once every 1 to 2 hours | 1 |
|  | voids more than once every hour | 2 |
| Urgency | urge to void equal to actual frequency | 0 |
|  | urge to void exceeds actual frequency | 1 |
|  | constant urge to void | 2 |
| Nocturia | no nocturia, or 1 void nightly | 0 |
|  | nocturia 2 to 4 times nightly | 1 |
|  | more than 4 times nightly | 2 |
| Dysuria | no dysuria | 0 |
|  | intermittent dysuria | 1 |
|  | dysuria with each void | 2 |
| Suprapubic pain (abdomino-perineal) | no pain | 0 |
|  | intermittent pain | 1 |
|  | constant pain | 2 |

At the time of diagnosis, and before any treatment, any patient who falls within the parameters of the inclusion of exclusion descriptors of the NIH workshop consensus criteria (above) will score at least a "4" on this survey (frequency<1; urgency<1; nocturia<1; and either dysuria or suprapubic pain<1).

Urine Collection: Urine specimens are collected from all patients before and during therapy. Voided urine is centrifuged at 1000×g for 10 minutes at 4° C. and the supernatant separated from the sediment. The urine supernatant is subjected to 0.2 l filtration (celluloseacetate) at 4° C. to remove any bacteria and debris, and a 1 ml aliquot is removed for creatinie measurement (CREATININE II ANALYZER™, Beckman Instruments, Inc., Brea, Calif.). The supernatant is ultrafiltered against 3× volume in phosphate-buffered saline (PBS) with 0.1 $\mu$g/ml albumin (Sigma, St. Louis, Mo.) using a filtration device (5,000 MW cut off; Amicon, Deavers, Mass.). The concentrated supernatant is dialyzed using 3,500 MW cutoff tubing, shell frozen with dry ice, and vacuum lyophilized. The powder is stored at −20° C.

Measurement of IL-2-IN Activity: The bioassay for IL2-IN is modified from the method for measuring IL-2 activity described by Gillis and associates. S. Gillis, et al., "T-Cell Growth Factor: Parameters Of Production And A Quantitative Microassay For Activity, *Journal of Immunology*, 120:2027, (1978). The murine IL-2-dependent cytotoxic T-cell line (CTLL-N) is derived from the CT-6 cell line. J. Kusugami, et al, "Intestinal Immune Reactivity To Interleukin-2 Differs Among Crohn's Disease, Ulcerative Colitis And Controls", *Gastroenterology*, 97:1 (1989). The CTLL-Ns are maintained in liquid culture using a 1:1 mixture of Roswell Park Memorial Institute (RPMI) 1640 and Dulbecco's Modified Eagles Medium (DMEM; 4.5 g/L glucose) media supplemented with 2.9 mg/ml glucose, 9.4 mM HEPES buffer, 1.9 mg/ml glutamine, 289 $\mu$g/ml arginine, 0.12 M non-essential amino acids, $5\times10^{-5}$ M 2-mercaptoethanol, 4.5% fetal bovine serum, 90 units/ml penicillin, 90 $\mu$g/ml streptomycin, 22 $\mu$g/ml fungizone, 0.45 mg/ml gentamicin and 20 units/ml of human recombinant IL-2.

The CTLL-Ns are washed and suspended at a concentration of $10^{-5}$/ml in the culture media. Assays are performed in triplicate, as follows: a serial dilution of the sample aliquot (50 $\mu$l), a 1:10 dilution of the human recombinant IL-2 standard and $10^{-4}$ CTLL-Ns (100 $\mu$l) are placed in microliter wells. The microliter plates are incubated in a humidified 6% $CO_2$ atmosphere at 37° C. for 24 hrs, and the cells are pulsed at the 19th hour with 1 $\mu$Ci/well of methyl-tritiated thymidine (specific activity 6.7 Ci/mM, New England Nuclear,I. E. Dupont, Boston, Mass.).

The cells are collected onto glass filter paper discs. The discs are placed in scintillation fluid and thymidine uptake is measured by liquid scintillation spectrophotometry. IL-2 inhibitory activity is calculated by modified probit analysis.

The proliferation "maximum" is the tritiated thymidine uptake caused by the amount of exogenous IL-2 activity in the control microliter wells, assessed in quadruplicate for each assay. The proliferation "minimum" is derived from lowest amount of tritiated thymidine uptake caused by the IL-2 inhibitor standard. The probit calculation corrected for minor interassay variations of thymidine uptake in control wells, and permitted interassay comparisons of inhibitor activity among the urine samples. By this treatment of the data, the calculated value of IL-2 inhibitory activity in lyophilized urine samples varies less than 10% from assay to assay. IL-2-IN activity is expressed in units/mg urine creatnine (U/mg u.c.). IL-2-IN activity is less than 0.05 U/mg u.c. in the urine of healthy adults. J. Fleischmann, et al., *Journal of Biological Reguators and Homeostatic Agents*, 4:73, (1990).

Medication Assignments: All patients are treated initially with a total daily dose of 30 mg, which is administered as a single, extended release tablet.

Patient Monitoring: Patients are interviewed and blood pressure measured twice monthly during the first 2 months of therapy, during the first 2 months after a dose escalation, and then once monthly thereafter. The symptom severity score at each interview is based on the patient's experiences during the previous 24 hours.

EXAMPLE 2

In addition to the treatment of patients with interstitial cystitis, patients with the urethral syndrome have been treated with a compound of Formula I, using the titration test and treatment protocol described in U.S. Pat. No. 5,145,859. Similar to the data of Example 1, the positive response to the compounds of the present invention in this limited study supports the hypothesis that the urethralsyndrome and interstitial cystitis are both part of the same disease spectrum, perhaps as variants of reflex sympathetic dystrophy.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See. e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| Active Ingredient(s) | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
| --- | --- |
| Active Ingredient(s) | 25.0 |
| Cellulose, microcrystalline | 200.0 |
| Colloidal silicon dioxide | 10.0 |
| Stearic acid 5.0 | |

The components are blended and compressed to form tablets, each weighing 240 mg.

Formulation Preparation 3

A dry powder inhaler formulation is prepared containing the following components:

| Ingredient | Weight % |
|---|---|
| Active Ingredient(s) | 5 |
| Lactose | 95 |

The active mixture is mixed with the lactose and the mixture is added to a dry powder inhaling appliance.

Tablets, each containing 30 mg of active ingredient, are prepared as follows:

| Ingredient | Quantity (mg/tablet) |
|---|---|
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
|---|---|
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient(s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with string. Sufficient water is then added to produce the required volume.

Formulation Preparation 8

Capsules, each containing 15 mg of medicament, are made as follows:

| Ingredient | Quantity (mg/capsule) |
|---|---|
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
|---|---|
| Active Ingredient(s) | 250.0 mg |
| Isotonic saline | 1000 ml |

Formulation Preparation 10

A topical formulation may be prepared as follows:

| Ingredient | Quantity |
|---|---|
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
|---|---|
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method for the treatment or prevention of interstitial cystitis or urethral syndrome in a mammal which comprise administering to a mammal in need thereof an effective amount of a compound of the formula

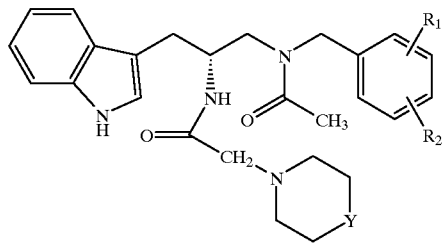

where $R^1$ and $R^2$ are independently selected from the group consisting of hydrogen, methyl, methoxy, chloro, and trifuoromethyl, with the proviso that no more than one of $R^1$ and $R^2$ can be hydrogen; and Y is

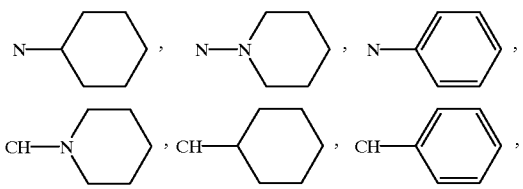

N—$R^a$, or CH—N$R^b R^c$, where $R^a$, $R^b$, and $R^c$ are independently selected from the group consisting of hydrogen and $C_1$–$C_6$ alkyl;

or a pharmaceutically acceptable salt or solvate thereof.

2. A method as claimed in claim 1 employing (R)-3-(1H-indol-3-yl)-1-[N-(2-methoxybenzyl)acetylamino]-2-[N-(2-(4-(piperidin-1-yl)piperidin-1-yl)acetyl)amino]propane or a pharmaceutically acceptable salt or solvate thereof.

3. A method as claimed in claim 2 employing (R)-3-(1H-indol-3-yl)-1-[N-(2-methoxybenzyl)acetylamino]-2-[N-(2-(4-(piperidin 1-yl)piperidin-1-yl)acetyl)amino]propane dihydrochloride trihydrate.

4. A pharmaceutical formulation containing, as an active ingredient, a compound as described in any one of claims 1 to 3, adapted for use in the treatment or prevention of interstitial cystitis or urethral syndrome.

* * * * *